US010772498B2

(12) United States Patent
Moriguchi

(10) Patent No.: US 10,772,498 B2
(45) Date of Patent: Sep. 15, 2020

(54) OPHTHALMOLOGICAL IMAGING DEVICE

(71) Applicant: TOPCON CORPORATION, Itabashi-ku, Tokyo (JP)

(72) Inventor: Yoshikiyo Moriguchi, Sendai (JP)

(73) Assignee: TOPCON CORPORATION, Itabashi-ku, Tokyo (JP)

( * ) Notice: Subject to any disclaimer, the term of this patent is extended or adjusted under 35 U.S.C. 154(b) by 206 days.

(21) Appl. No.: 15/768,851

(22) PCT Filed: Oct. 19, 2016

(86) PCT No.: PCT/JP2016/080886
§ 371 (c)(1),
(2) Date: Apr. 17, 2018

(87) PCT Pub. No.: WO2017/073412
PCT Pub. Date: May 4, 2017

(65) Prior Publication Data
US 2018/0353067 A1  Dec. 13, 2018

(30) Foreign Application Priority Data
Oct. 29, 2015  (JP) ................................ 2015-212804

(51) Int. Cl.
*A61B 3/10*  (2006.01)
*A61B 3/14*  (2006.01)

(52) U.S. Cl.
CPC ............... *A61B 3/102* (2013.01); *A61B 3/14* (2013.01)

(58) Field of Classification Search
CPC ......... A61B 3/1225; A61B 3/14; A61B 3/102; A61B 3/0025

(Continued)

(56) References Cited

U.S. PATENT DOCUMENTS 5,727,551 A * 3/1998 Takagi .................. A61B 3/165
                                                            600/398
7,387,394 B2 * 6/2008 Minegishi .............. A61B 3/103
                                                            359/846

(Continued)

FOREIGN PATENT DOCUMENTS

JP  2012-061349 A  3/2012
JP  2012-213617 A  11/2012
JP  2015-029834 A  2/2015

OTHER PUBLICATIONS

International Search Report dated Dec. 13, 2016, in connection with International Patent Application No. PCT/JP2016/080886, 3 pgs.

*Primary Examiner* — Wen Huang
(74) *Attorney, Agent, or Firm* — Chiesa Shahinian & Giantomasi PC

(57) ABSTRACT

An ophthalmological imaging device according to embodiments comprises an objective lens, an interference optical system, an optical scanner, a controller, and an image forming part. The interference optical system divides light from a light source into measurement light and reference light, causes the measurement light to become incident on a subject's eye via the objective lens, and detects interference light between the reference light and return light of the measurement light that has exited from the subject's eye and passed through the objective lens. The optical scanner deflects the measurement light. The controller controls the optical scanner such that a position away from an optical axis of the objective lens is set as a center to deflect the measurement light. The image forming part forms an image of the subject's eye based on a detection result of the interference light by the interference optical system.

5 Claims, 8 Drawing Sheets

(58) Field of Classification Search
USPC .......................................................... 351/206
See application file for complete search history.

(56) References Cited

U.S. PATENT DOCUMENTS

| | | | | |
|---|---|---|---|---|
| 7,568,800 | B2* | 8/2009 | Mihashi | A61B 3/10 |
| | | | | 351/206 |
| 7,850,305 | B2* | 12/2010 | Hirohara | A61B 5/14555 |
| | | | | 351/206 |
| 7,980,696 | B1* | 7/2011 | Taki | A61B 3/102 |
| | | | | 351/205 |
| 2012/0250029 | A1 | 10/2012 | Yoshida | |
| 2014/0029015 | A1 | 1/2014 | Schmoll et al. | |
| 2015/0042951 | A1* | 2/2015 | Stanga | A61B 3/0025 |
| | | | | 351/206 |
| 2015/0094978 | A1* | 4/2015 | Hanebuchi | G01B 9/02069 |
| | | | | 702/106 |
| 2015/0138502 | A1* | 5/2015 | Moriguchi | A61B 3/14 |
| | | | | 351/206 |
| 2015/0313467 | A1* | 11/2015 | Sakai | A61B 3/102 |
| | | | | 351/208 |
| 2017/0042419 | A1* | 2/2017 | Nakanishi | A61F 9/007 |

* cited by examiner

OPHTHALMOLOGICAL IMAGING DEVICE

CROSS-REFERENCE TO RELATED APPLICATIONS

This application is a national stage (under 35 U.S.C. 371) of International Patent Application No. PCT/JP2016/080886, filed Oct. 19, 2016, claiming priority to Japanese Patent Application No. 2015-212804, filed Oct. 29, 2015, both of which are herein incorporated by reference in their entirety.

FIELD

Embodiments described herein relates to an ophthalmological imaging device.

BACKGROUND

An optical coherence tomography (OCT, hereafter) is used for forming an image representing a surface morphology and internal morphology of an object to be measured. An artifact due to a reflection from an object other than the object to be measured or a phenomenon of coherence revival may appear in an OCT image acquired by using OCT. Their artifacts may appear overlapping with the attention site or affect a result of image processing such as a segmentation processing, or the like.

For example, an artifact due to a reflection from the object other than the object to be measured may be removed by applying an anti-reflection coating to an optical member constituting an interference optical system for acquiring the OCT image. Also, a method to remove an artifact by performing phase modulation with respect to light from a light source so as to suppress occurrence of the phenomenon of coherence revival is known (U.S. Unexamined Patent Application Publication No. 2014/0029015).

However, even if the anti-reflection coating is applied to the optical member, it is difficult to suppress the reflection perfectly. In addition, in the method disclosed in U.S. Unexamined Patent Application Publication No. 2014/0029015, design depending on an optical condition such as kinds or placement of the optical member constituting the optical system is needed, and thereby this makes it complicated to design the optical system and a control system.

In general, artifacts due to the reflection from the object other than the object to be measured are more likely to appear in the OCT image as coherence length becomes longer. Furthermore, artifacts due to the phenomenon of coherence revival are more likely to appear in the OCT image as interval of coherence revival becomes shorter. Therefore, in case of using a light source of which coherence length is long or a light source of which interval of coherence revival is short, deterioration of the OCT image is more likely to occur, and thereby a new technology is required to remove the artifact described above.

SUMMARY

The present invention is made to solve the aforementioned problem, and the object thereof is to provide a novel technology for removing artifacts appeared in an image acquired by using an interference optical system.

An ophthalmological imaging device of the embodiments comprises an objective lens, an interference optical system, an optical scanner, a controller, and an image forming part. The interference optical system divides light from a light source into measurement light and reference light, causes the measurement light to become incident on a subject's eye via the objective lens, and detects interference light between the reference light and return light of the measurement light that has exited from the subject's eye and passed through the objective lens. The optical scanner deflects the measurement light. The controller controls the optical scanner such that a position away from an optical axis of the objective lens is set as a center to deflect the measurement light. The image forming part forms an image of the subject's eye based on a detection result of the interference light by the interference optical system.

According to the embodiments, a novel technology for removing artifacts appeared in an image acquired by using an interference optical system can be provided.

DETAILED DESCRIPTION

Figure 1:
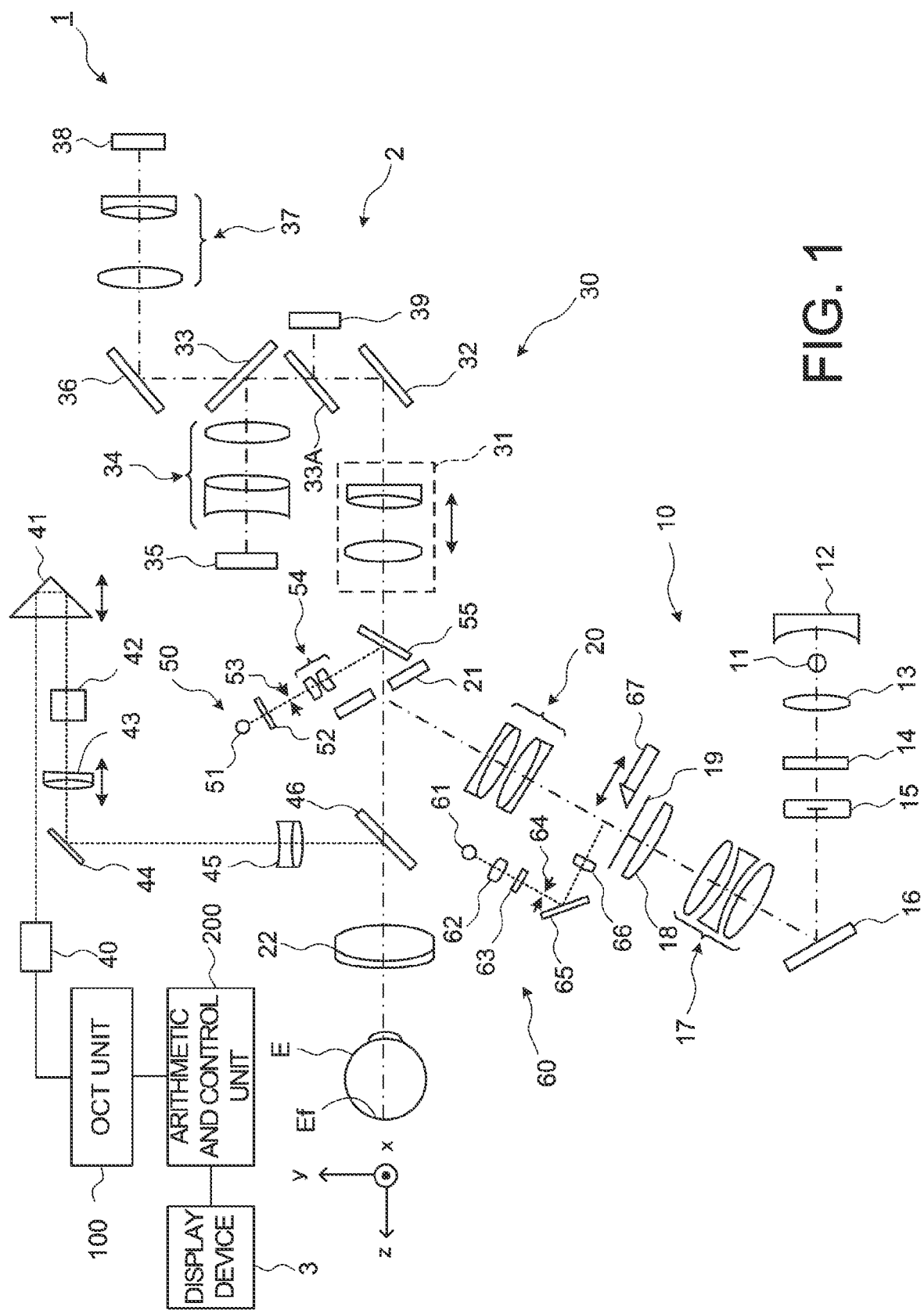
FIG. 1 is a schematic diagram illustrating an example of a configuration of an ophthalmological imaging device according to embodiments.

Exemplary embodiments of the present invention will be described in detail with referring to the drawings. An ophthalmological imaging device according to the present invention has a function of an optical coherence tomography apparatus and performs optical coherence tomography on a subject's eye. The OCT is performed on an arbitrary site of the subject's eye, for example, on the fundus or on the anterior segment.

In this specification, images acquired by OCT may be collectively referred to as OCT images. Further, in some cases in the following description, noise and artifacts may be treated in the same way and represented noise as artifacts. In addition, the contents of the documents cited in the specification can be incorporated as contents of the following embodiments.

The following embodiments describe an ophthalmological imaging device capable of performing Fourier-domain-type OCT. For example, the ophthalmological imaging device according to the embodiments may be configured to perform swept-source-type OCT. It should be noted that the configuration according to the present embodiments can also be applied to an ophthalmological imaging device capable of performing OCT of other type than the swept source OCT such as spectral domain OCT. In addition, the following embodiments describe an apparatus in which an OCT apparatus and a fundus camera are combined. However, it is also possible to combine an OCT apparatus that has the configuration according to the embodiments with a modality other than the fundus camera, for example, a scanning laser ophthalmoscope (SLO), a slit lamp microscope, an ophthalmic surgical microscope, a photocoagulation apparatus, or the like. Alternatively, the configuration of the embodiments may be applied to a single-functional OCT device.

[Configuration]

As shown in FIG. 1, the ophthalmological imaging device 1 includes a fundus camera unit 2, an OCT unit 100, and an arithmetic and control unit 200. The fundus camera unit 2 has substantially the same optical system as the conventional fundus camera. The OCT unit 100 is provided with an optical system for performing OCT. The arithmetic and control unit 200 is provided with a computer for performing various arithmetic processes and control processes.

[Fundus Camera Unit]

As illustrated in FIG. 1, the fundus camera unit 2 is provided with an optical system for acquiring two-dimensional images (fundus images) rendering the surface morphology of a fundus Ef of a subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. Further, the fundus camera unit 2 is provided with an illumination optical system 10 and an imaging optical system 30. The illumination optical system 10 projects illumination light onto the fundus Ef. The imaging optical system 30 guides the illumination light reflected from the fundus to imaging devices (CCD image sensors 35 and 38, sometimes simply referred to as "CCD"). Further, the imaging optical system 30 guides measurement light coming from the OCT unit 100 to the subject's eye E, and guides the measurement light returning from the subject's eye E to the OCT unit 100.

An observation light source 11 of the illumination optical system 10 includes, for example, a halogen lamp or a light emitting diode (LED). Light (observation illumination light) emitted from the observation light source 11 is reflected by a reflection mirror 12 having a curved reflective surface, and becomes near-infrared light after penetrating a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding area of an aperture part) of an aperture mirror 21, penetrates a dichroic mirror 46, and refracted by an objective lens 22, thereby illuminating the fundus Ef.

The observation illumination light reflected from the fundus is refracted by the objective lens 22, penetrates the dichroic mirror 46, passes through the aperture part formed in the center area of the aperture mirror 21, penetrates a dichroic mirror 55, travels through a focusing lens 31, and is reflected by a mirror 32. Further, the fundus reflection light penetrates a half mirror 33A, is reflected by a dichroic mirror 33, and forms an image on the light receiving surface of the CCD image sensor 35 by a condenser lens 34. The CCD image sensor 35 detects the fundus reflection light at a predetermined frame rate, for example. An image (observation image) based on the fundus reflection light detected by the CCD image sensor 35 is displayed on a display device 3. Note that when the imaging optical system 30 is focused on the anterior segment, an observation image of the anterior segment of the subject's eye E is displayed.

The imaging light source 15 is formed of, for example, a xenon lamp or an LED. The light (imaging illumination light) output from the imaging light source 15 is projected onto the fundus Ef via the same route as that of the observation illumination light. The fundus reflection light of the imaging illumination light is guided to the dichroic mirror 33 via the same route as that of the observation illumination light, penetrates the dichroic mirror 33, is reflected by a mirror 36, and forms an image on the light receiving surface of the CCD image sensor 38 by a condenser lens 37. The display device 3 displays an image (photographed image) based on the fundus reflection light detected by the CCD image sensor 38. Note that the same device or different devices may be used as the display device 3 for displaying an observation image and the display device 3 for displaying a photographed image. Besides, when similar photographing is performed by illuminating the subject's eye E with infrared light, an infrared photographed image is displayed. An LED may be used as the imaging light source.

A liquid crystal display (LCD) 39 displays a fixation target or a visual target for measuring visual acuity. The fixation target is an indicator for fixating the subject's eye E, and is used when performing fundus photography and OCT measurement.

Part of the light output from the LCD 39 is reflected by the half mirror 33A, reflected by the mirror 32, travels through the focusing lens 31 and the dichroic mirror 55, passes through the aperture part of the aperture mirror 21, penetrates the dichroic mirror 46, and is refracted by the objective lens 22, thereby being projected onto the fundus Ef. By changing the display position of the fixation target on the screen of the LCD 39, the fixation position of the subject's eye E can be changed.

Further, as with conventional fundus cameras, the fundus camera unit 2 is provided with an alignment optical system 50 and a focus optical system 60. The alignment optical system 50 generates an indicator (an alignment indicator) for the position matching (the alignment) of the optical system with respect to the subject's eye E. The focus optical system 60 generates an indicator (a split indicator) for adjusting the focus with respect to the subject's eye E.

The light (alignment light) output from an LED 51 of the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the subject's eye E by the objective lens 22.

Cornea reflection light of the alignment light travels through the objective lens 22, the dichroic mirror 46 and the abovementioned aperture part. Part of the cornea reflection light penetrates the dichroic mirror 55, passes through the focusing lens 31, is reflected by the mirror 32, penetrates the half mirror 33A, is reflected by the dichroic mirror 33, and is projected onto the light receiving surface of the CCD image sensor 35 by the condenser lens 34. A light receiving image (an alignment indicator) captured by the CCD image sensor 35 is displayed on the display device 3 together with the observation image. A user conducts alignment by the same operation as performed on a conventional fundus camera. Instead, alignment may be performed in such a way that the arithmetic and control unit 200 analyzes the position of the alignment indicator and moves the optical system (automatic alignment).

To conduct focus adjustment, a reflective surface of a reflection rod 67 is arranged in a slanted position on an optical path of the illumination optical system 10. The light (focus light) output from an LED 61 of the focus optical system 60 passes through a relay lens 62, is split into two light beams by a split indicator plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the aperture mirror 21, penetrates the dichroic mirror 46, and is refracted by the objective lens 22, thereby being projected onto the fundus Ef.

Fundus reflection light of the focus light passes through the same route as the cornea reflection light and is detected by the CCD image sensor 35. The display device 3 displays the light receiving image (split indicator) captured by the CCD image sensor 35 together with the observation image. As in the conventional case, the arithmetic and control unit 200 analyzes the position of the split indicator, and moves the focusing lens 31 and the focus optical system 60 for focusing (automatic focusing). Alternatively, the user may perform the focusing manually while visually checking the split indicator.

The dichroic mirror 46 branches an optical path for OCT from an optical path for fundus photography. The dichroic mirror 46 reflects light of wavelength band used in OCT, and transmits light for fundus photography. The optical path for OCT is provided with, in order from the OCT unit 100 side, a collimator lens unit 40, an optical path length changing part 41, an optical scanner 42, a focusing lens 43, a mirror 44, and a relay lens 45.

The optical path length changing part 41 is movable in directions indicated by the arrow in FIG. 1, thereby changing the optical length of the optical path for OCT. This change in the optical path length is used for correcting the optical path length according to the axial length of the subject's eye E, adjusting the interference state, and the like. The optical path length changing part 41 includes, for example, a corner cube and a mechanism for moving the corner cube.

The optical scanner 42 is disposed at a position optically conjugate with the pupil of the subject's eye E. The optical scanner 42 changes the traveling direction of the light (measurement light LS) passing through the OCT optical path. Thereby, the subject's eye E can be scanned with the measurement light LS. The optical scanner 42 includes, for example, a galvano mirror that deflects the measurement light LS in the x direction, a galvano mirror that deflects the measurement light LS in the y direction, and a mechanism(s) that independently drives the galvano mirrors. Thereby, it is possible to scan the measurement light LS in an arbitrary direction in the xy plane.

[OCT Unit]

Figure 2:
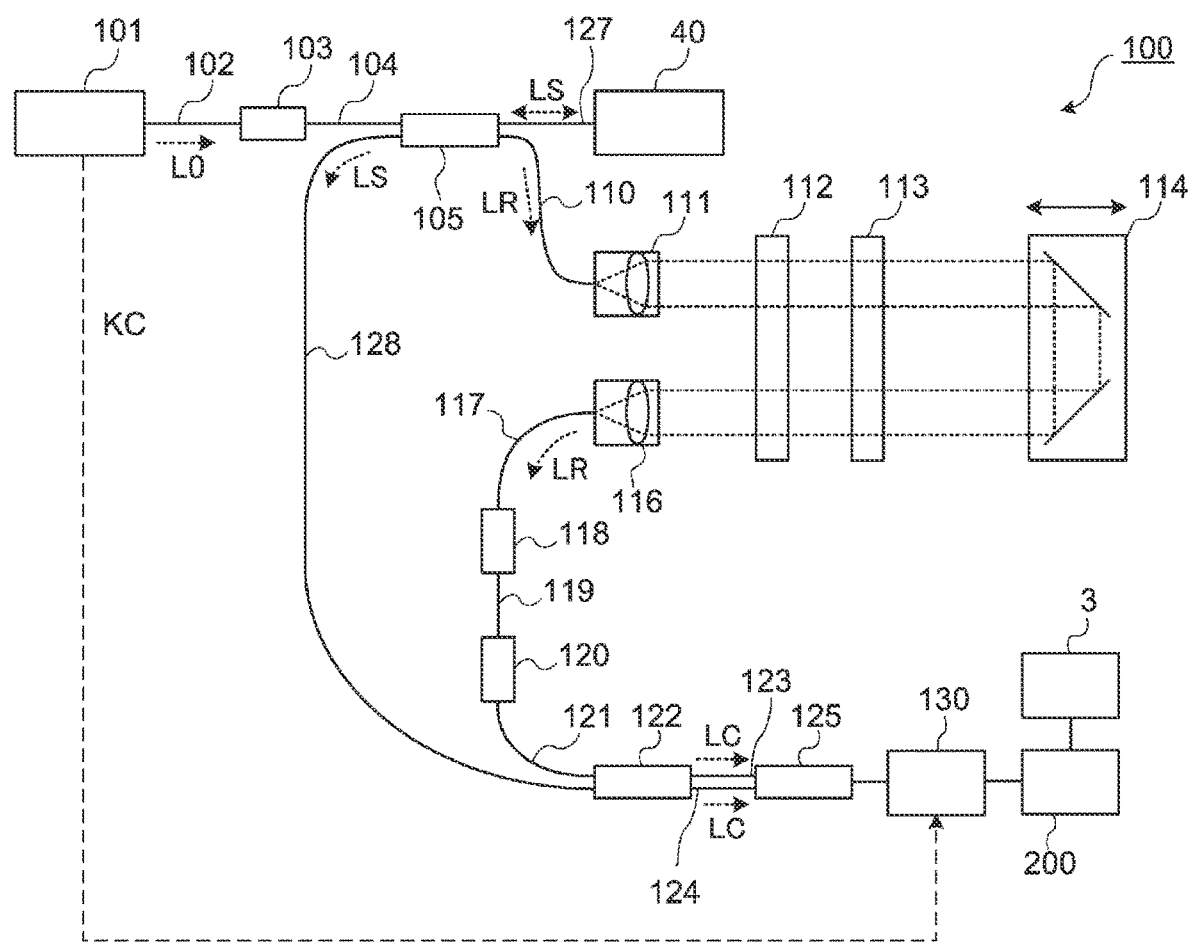
FIG. 2 is a schematic diagram illustrating an example of the configuration of the ophthalmological imaging device according to the embodiments.

Exemplary configuration of the OCT unit 100 is shown in FIG. 2. The OCT unit 100 is provided with an optical system for acquiring OCT images of the subject's eye E. The optical system has a similar configuration to a conventional swept-source-type OCT apparatus. That is, the optical system is an interference optical system that splits the light from the wavelength tunable type (wavelength scanning type) light source into the measurement light and a reference light, make the measurement light returning from the subject's eye E and the reference light having traveled through a reference optical path interfere with each other to generate interference light, and to detect the interference light. The detection result (detection signal) of the interference light obtained by the interference optical system is a signal indicating a spectrum of the interference light, and is sent to the arithmetic and control unit 200.

Like general swept-source-type OCT apparatuses, the light source unit 101 includes a wavelength tunable type (a wavelength scanning type) light source capable of sweeping (scanning) the wavelengths of emitted light. The wavelength tunable type light source includes a laser light source that includes a resonator. The light source unit 101 temporally changes the output wavelengths within the near infrared wavelength bands that cannot be visually recognized with human eyes.

The light L0 output from the light source unit 101 is guided to a polarization controller 103 through an optical fiber 102 and the polarization state thereof is adjusted. The polarization controller 103, for example, applies external stress to the looped optical fiber 102 to thereby adjust the polarization state of the light L0 guided through the optical fiber 102.

The light L0 whose polarization state has been adjusted by the polarization controller 103 is guided to a fiber coupler 105 through an optical fiber 104 and is split into the measurement light LS and the reference light LR.

The reference light LR is guided to a collimator 111 through an optical fiber 110 and becomes a parallel light beam. The reference light LR, which has become the parallel light beam, is guided to the corner cube 114 via the optical path length correction member 112 and the dispersion compensation member 113. The optical path length correction member 112 functions as a delay means to match the optical path length (optical distance) of the reference light LR and the optical path length of the measurement light LS. The dispersion compensation member 113 functions as a dispersion compensating means to match the dispersion characteristics of the reference light LR and the measurement light LS.

The corner cube 114 changes the traveling direction of the reference light LR that has become a parallel light beam by the collimator 111 in the opposite direction. The optical path of the reference light LR incident on the corner cube 114 and the optical path of the reference light LR emitted from the corner cube 114 are parallel. Further, the corner cube 114 is movable in a direction along the incident light path and the emitting light path of the reference light LR. Through this movement, the length of the optical path of the reference light LR is changed.

The configuration shown in FIG. 1 and FIG. 2 include both the optical path length changing part 41 that changes the length of the optical path (measurement optical path, measurement arm) of the measurement light LS and the corner cube 114 that changes the length of the optical path (reference optical path, reference arm) of the reference light LR. However, the ophthalmological imaging device may include any one of the optical path length changing part 41 and the corner cube 114. The ophthalmological imaging device can also change the difference between the measurement optical path length and the reference optical path length by using other optical members.

The reference light LR that has been reflected by the corner cube 114 travels through the dispersion compensation member 113 and the optical path length correction member 112, and is converted from the parallel light flux into a converging light flux by a collimator 116, and enters an optical fiber 117. The reference light LR is guided to a polarization controller 118, and thereby its polarization state is adjusted.

The polarization controller 118 has the same configuration as, for example, the polarization controller 103. The reference light LR whose polarization state has been adjusted by the polarization controller 118 is guided to an attenuator 120 through an optical fiber 119 and the light amount is adjusted under the control of the arithmetic and control unit 200. The reference light LR whose light amount is adjusted by the attenuator 120 is guided to a fiber coupler 122 through an optical fiber 121.

Meanwhile, the measurement light LS generated by the fiber coupler 105 is guided through an optical fiber 127, and is made into a parallel light beam by the collimator lens unit 40. The measurement light LS made into a parallel light beam reaches the dichroic mirror 46 via the optical path length changing part 41, the optical scanner 42, the focusing lens 43, the mirror 44, and the relay lens 45. Then, the measurement light LS is reflected by the dichroic mirror 46, refracted by the objective lens 22, and irradiated onto the subject's eye E. The measurement light LS is scattered (and reflected) at various depth positions of the subject's eye E. The returning light of the measurement light LS including such backscattered light advances through the same path as the outward path in the opposite direction and is guided to the fiber coupler 105, and then reaches the fiber coupler 122 through an optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 are guided to a detector 125 through optical fibers 123 and 124, respectively.

The detector 125 is, for example, a balanced photodiode that includes a pair of photodetectors for respectively detecting the pair of the interference light LC and outputs the difference between the pair of detection results obtained by the pair of photodetectors. The detector 125 sends the detection result (detection signal) to a DAQ (data acquisition system) 130. A clock KC is supplied from the light source unit 101 to the DAQ 130. The clock KC is generated in the light source unit 101 in synchronization with the output timing of each wavelength sweeping (scanning) within a predetermined wavelength range performed by the wavelength tunable type light source. For example, the light source unit 101 optically delays one of the two pieces of branched light obtained by branching the light L0 of each output wavelength, and then generates the clock KC based on the result of the detection of the combined light of the two pieces of branched light. The DAQ 130 performs the sampling of the detection result obtained by the detector 125 based on the clock KC. The DAQ 130 sends the result of the sampling of the detection result obtained by the detector 125 to the arithmetic and control unit 200. For example, the arithmetic and control unit 200 performs the Fourier transform etc. on the spectral distribution based on the detection result obtained by the detector 125 for each series of wavelength scanning (i.e., for each A line). With this, the reflection intensity profile for each A line is formed. In addition, the arithmetic and control unit 200 forms image data by applying imaging processing to the reflection intensity profiles of the respective A lines.

[Arithmetic and Control Unit]

The configuration of the arithmetic and control unit 200 will be described. The arithmetic and control unit 200 analyzes a detection signal input from the detector 125 to form an OCT image of the subject's eye E. The arithmetic processing for the OCT image formation is performed in the same manner as in the conventional swept-source-type OCT apparatus.

Further, the arithmetic and control unit 200 controls the fundus camera unit 2, the display device 3, and the OCT unit 100. For example, the arithmetic and control unit 200 controls the display device 3 to display the OCT image of the subject's eye E.

The arithmetic and control unit 200 includes a processor, a random access memory (RAM), a read only memory (ROM), a hard disk drive, a communication interface, and the like. In addition, the arithmetic and control unit 200 may include an operation device (input device) such as a keyboard and a mouse, and a display device such as an LCD. The processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). A storage device such as the hard disk drive stores a computer program for controlling the ophthalmological imaging device 1. For example, the arithmetic and control unit 200 reads a program stored in a memory circuit or a storage device and executes it, thereby implementing the functions according to the embodiments.

[Control System]

Figure 3:
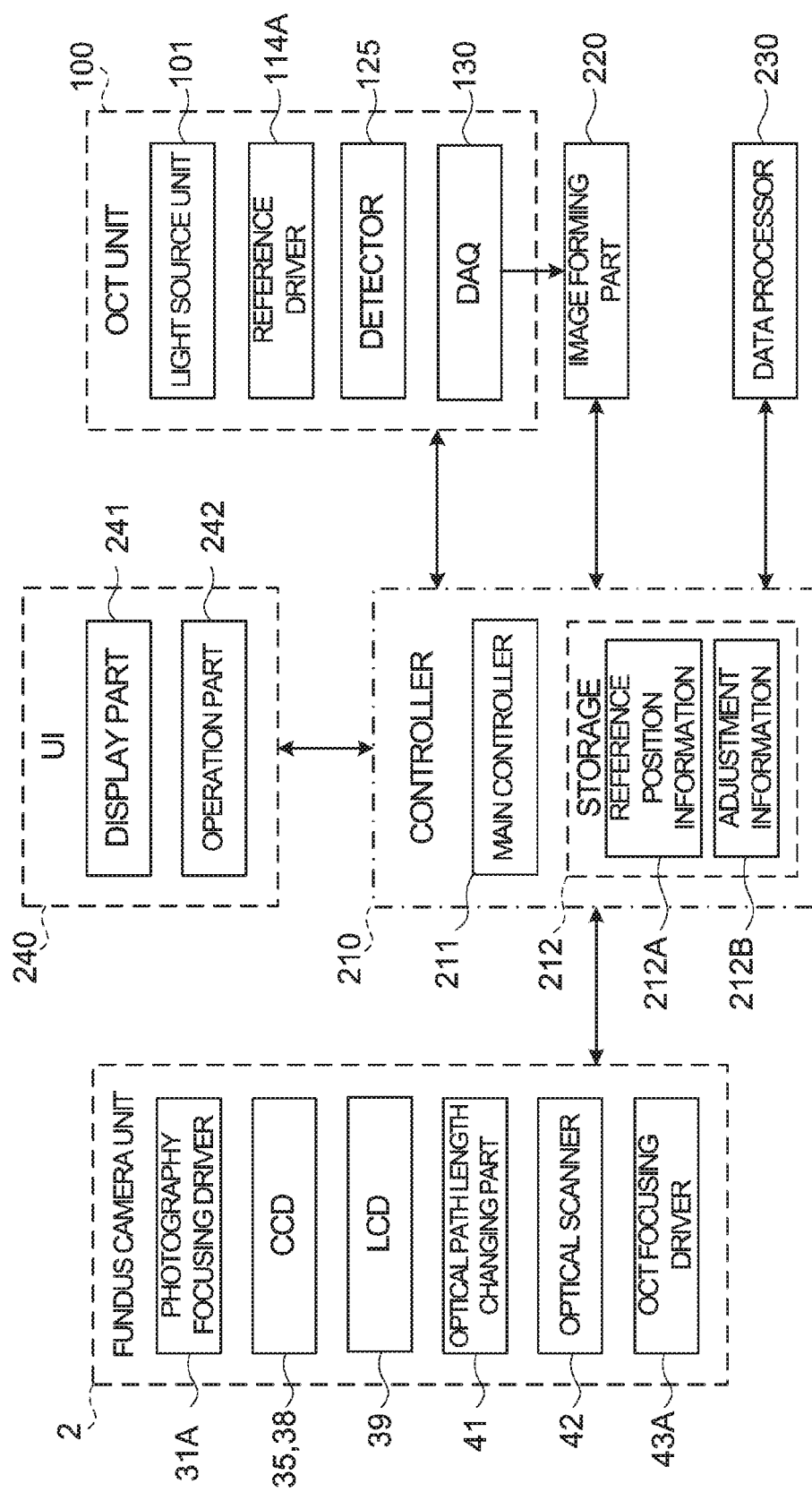
FIG. 3 is a schematic diagram illustrating an example of the configuration of the ophthalmological imaging device according to the embodiments.

The configuration of the control system of the ophthalmological imaging device 1 will be described with referring to FIG. 3. In FIG. 3, some components of the ophthalmological imaging device 1 are omitted, and particularly necessary components are selectively shown for describing the present embodiment.

(Controller)

The controller 210 is the center of the control system of the ophthalmological imaging device 1. The controller 210 includes, for example, the aforementioned processor, RAM, ROM, hard disk drive, communication interface, and the like. The controller 210 is provided with a main controller 211 and a storage 212.

(Main Controller)

The main controller 211 performs the various kinds of controls described above. In particular, as shown in FIG. 3, the main controller 211 controls a photography focusing driver 31A, the CCD image sensors 35 and 38, the LCD 39, the optical path length changing part 41, the optical scanner 42, an OCT focusing driver 43A, and the like of the fundus camera unit 2. Further, the main controller 211 controls components of the OCT unit 100 such as the light source unit 101, the reference driver 114A, the detector 125, and the DAQ 130.

The photography focusing driver 31A moves the focusing lens 31 in the optical axis direction. With this, the focus position of the imaging optical system 30 is changed. Incidentally, the main controller 211 may control an optical system driver (not illustrated) to three dimensionally move the optical system provided in the fundus camera unit 2. This control is used in alignment and tracking. Here, tracking is to move the optical system of the device according to the movement of the subject's eye E. To perform tracking, alignment and focusing are performed in advance. The tracking is performed by moving the optical system of the device in real time according to the position and orientation of the subject's eye E based on the moving image obtained by imaging the subject's eye E, thereby maintaining a suitable positional relationship in which alignment and focusing are adjusted.

The OCT focusing driver 43A moves the focusing lens 43 along the optical axis of the measurement optical path. Thereby, the focus position of the measurement light LS is changed. The focus position of the measurement light LS corresponds to the depth position (z position) of the beam waist of the measurement light LS.

The reference driver 114A moves the corner cube 114 provided in the reference optical path. Thereby, the length of the reference light path is changed. As described above, the ophthalmological imaging device 1 may include any one of the optical path length changing part 41, and the corner cube 114 and the reference driver 114A.

The main controller 211 controls the LCD 39 by designating a desired position in a fixation target coordinate system to change the display position of the fixation target on the screen of the LCD 39. The fixation target coordinate system is a two-dimensional orthogonal coordinate system (xy coordinate system) associated with a coordinate system defined to the screen of the LCD 39. The main controller 211 can change a relative position of the fixation target coordinate system with respect to an optical axis of the objective lens 22.

For example, the main controller 211 changes the relative position of the fixation target coordinate system with respect to the optical axis of the objective lens 22, by controlling the display position of the fixation target on the LCD 39 so that the desired position in a predetermined control coordinate system (device coordinate system) is located at an origin of the fixation target coordinate system. In this case, the storage 212 previously stores reference position information 212A for setting the origin of the fixation target coordinate system to an initial position (X0,Y0) in the control coordinate system. For example, the initial position (X0,Y0) is a position on the optical axis of the objective lens 22. Further, the storage 212 afterwards stores the adjustment information 212B including amount of offset ($\Delta$x0,$\Delta$y0) in the both axis directions, which is obtained by adjusting the origin position of the fixation target coordinate system in a shipping process or a maintenance process. The main controller 211 reads out the reference position information 212A and the adjustment information 212B from the storage 212 and controls the display position of the fixation target on the LCD 39 so that a new position (X0+$\Delta$x0,Y0+$\Delta$y0) is located at the origin of the fixation target coordinate system. That is, the main controller 211 can control the LCD 39 by changing to the fixation target coordinate system with a position away from the optical axis of the objective lens 22 as the control center.

Further, the main controller 211 changes a scan position or a scan area of the measurement light LS, by controlling the optical scanner 42 by designating a desired position in a scanner coordinate system. The scanner coordinate system is a two-dimensional orthogonal coordinate system (xy coordinate system) associated with a coordinate system defined with respect to a measurement site of the subject's eye E. The main controller 211 can change a relative position of the scanner coordinate system with respect to the optical axis of the objective lens 22.

For example, the main controller 211 changes the relative position of the scanner coordinate system with respect to the optical axis of the objective lens 22, by controlling the scan position with respect to the subject's eye E so that the desired position in a predetermined control coordinate system is located at an origin of the scanner coordinate system. In this case, the storage 212 previously stores reference position information 212A for setting the origin of the scanner coordinate system to an initial position (X1,Y1) in the control coordinate system. For example, the initial position (X1,Y1) is a position on the optical axis of the objective lens 22 (X0=X1 and Y0=Y1). Further, the storage 212 afterwards stores the adjustment information 212B including amount of offset ($\Delta$x1, $\Delta$y1) in the both axis directions, which is obtained by adjusting the origin position of the scanner coordinate system in the shipping process or the maintenance process. The main controller 211 reads out the reference position information 212A and the adjustment information 212B from the storage 212 and controls the scan position with respect to the subject's eye E so that a new position (X1+$\Delta$x1,Y1+$\Delta$y1) is located at the origin of the scanner coordinate system. That is, the main controller 211 can control the optical scanner 42 to deflect the measurement light LS with a position away from the optical axis of the objective lens 22 as the control center.

The main controller 211 can change the relative position of the fixation target coordinate system with respect to subject's eye E in conjunction with changing the relative position of the scanner coordinate system described above. For example, the main controller 211 changes the relative positions of the both coordinate systems with respect to the optical axis of the objective lens 22 with the same amount of offset ($\Delta$x0=$\Delta$x1, $\Delta$y0=$\Delta$y1) included in the adjustment information 212B. That is, the main controller 211 can change a position of the fixation target coordinate system according to a displacement of the control center of the optical scanner 42 from the optical axis O of the objective lens 22. Further, for example, the initial positions of the both coordinate systems included in the reference position information 212A may be same (X0=X1 and Y0=Y1) and the amount of offset of the both coordinate systems may be the same ($\Delta$x0=$\Delta$x1, $\Delta$y0=$\Delta$y1). Thereby, the main controller 211 can change the relative positions of the both coordinate systems with respect to the optical axis of the objective lens 22 with the origin of the fixation target coordinate system coinciding with the origin of the scanner coordinate system.

Alternatively, the main controller 211 may change the relative position of the fixation target coordinate system with respect to the optical axis of the objective lens 22, independently of changing the relative position of the scanner coordinate system described above.

(Storage)

The storage 212 stores various types of data. Examples of the data stored in the storage 212 include, for example, image data of an OCT image, image data of a fundus image, subject's eye information, and the like, other than the reference position information 212A and the adjustment information 212B described above. The subject's eye information includes information on the subject such as patient ID and name, and information on the subject's eye such as identification information of the left eye/right eye. In addition, the storage 212 stores various types of programs and data to run the ophthalmological imaging device 1.

(Image Forming Part)

An image forming part 220 forms image data of a tomographic image of the fundus Ef based on detection signals from the detector 125 (DAQ 130). That is, the image forming part 220 forms the image data of the subject's eye E based on a detection result of the interference light LC obtained by the interference optical system. As in the conventional swept-source-type OCT, the image formation process includes filtering, fast Fourier transform (FFT), and the like. The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

The image forming part 220 includes, for example, the circuitry described above. Incidentally, "image data" and an "image" based thereon may be treated in the same way in this specification. Further, a site of the subject's eye E and an image thereof may also be treated in the same way.

(Data Processor)

A data processor 230 performs various types of data processing (image processing) and various types of analysis on an OCT image formed by the image forming part 220. For example, the data processor 230 performs various correction processes such as brightness correction and dispersion correction of images. The data processor 230 performs various types of image processing and analysis on images (fundus image, anterior segment image, etc.) captured by the fundus camera unit 2.

The data processor 230 can form volume data (voxel data) of the subject's eye E by performing known image processing such as interpolation processing for interpolating pixels between cross sectional images. In the case of displaying an image based on the volume data, the data processor 230 performs a rendering process on the volume data so as to form a pseudo three-dimensional image viewed from a specific line-of-sight direction.

The data processor 230 can perform position matching between a fundus image and an OCT image. When the fundus image and the OCT image are obtained in parallel, the position matching between the fundus image and the OCT image, which have been (almost) simultaneously obtained, can be performed using the optical axis of the imaging optical system 30 as a reference. Such position matching can be achieved since the optical system for the fundus image and that for the OCT image are coaxial. Besides, regardless of the timing of obtaining the fundus image and that of the OCT image, the position matching between the fundus image and the OCT image can be achieved by performing the position matching between the fundus image with a front image formed by projecting at least part of the image area in the OCT image corresponding to the fundus Ef onto the xy plane. This position matching method can also be employed when the optical system for acquiring fundus image and the optical system for OCT are not coaxial. Further, when both the optical systems are not coaxial, if the relative positional relationship between these optical systems is known, the position matching can be performed with referring to the relative positional relationship in a manner similar to the case of coaxial optical systems.

The data processor 230 that functions as above includes, for example, a processor, a RAM, a ROM, a hard disk drive, a circuit board, and the like. In a storage device such as the hard disk drive, a computer program for causing the processor to execute the functions described above is stored in advance.

(User Interface)

A user interface 240 includes the display part 241 and an operation part 242. The display part 241 includes the aforementioned display device of the arithmetic and control unit 200 and the display device 3. The operation part 242 includes the aforementioned operation device of the arithmetic and control unit 200. The operation part 242 may include various kinds of buttons and keys provided on the housing of the ophthalmological imaging device 1, or provided outside the ophthalmological imaging device 1. Further, the display part 241 may include various kinds of display devices, such as a touch panel placed on the housing of the fundus camera unit 2.

Note that the display part 241 and the operation part 242 need not necessarily be formed as separate devices. For example, a device like a touch panel, which has a display function integrated with an operation function, can be used. In such a case, the operation part 242 includes the touch panel and a computer program. The content of an operation performed using the operation part 242 is fed to the controller 210 as an electrical signal. Moreover, operations and inputs of information may be performed using a graphical user interface (GUI) displayed on the display part 241 and the operation part 242.

The combination of the OCT unit 100, the collimator lens unit 40, the optical path length changing part 41, the optical scanner 42, the focusing lens 43, the mirror 44 and the relay lens 45 is an example of the "interference optical system" according to the embodiments. The combination of the LCD 39, the half mirror 33A, the mirror 32, the focusing lens 31, the dichroic mirror 55, the aperture mirror 21, and the dichroic mirror 46 is an example of the "fixation target projection system" according to the embodiments. The LCD 39 is an example of the "light emitting part configured to be capable of changing a light emitting position". The reference position information 212A is an example of the "light emitting position information".

OPERATION EXAMPLE

The operation of the ophthalmological imaging device 1 will be described.

Figure 4A:
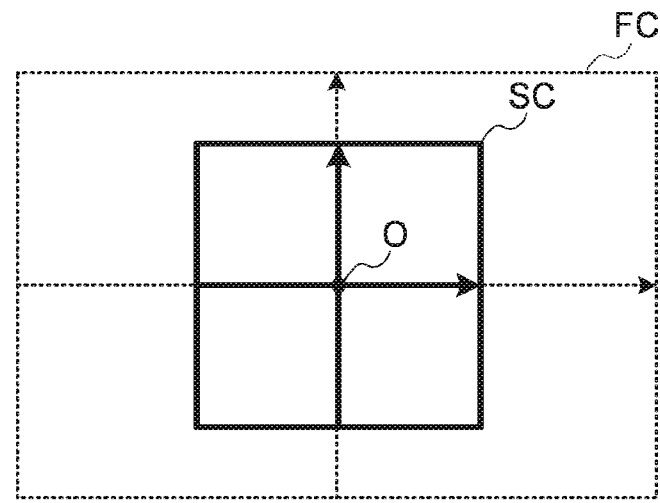
FIG. 4A is a schematic diagram for describing an operation of the ophthalmological imaging device according to comparative examples of the embodiments.
Figure 4B:
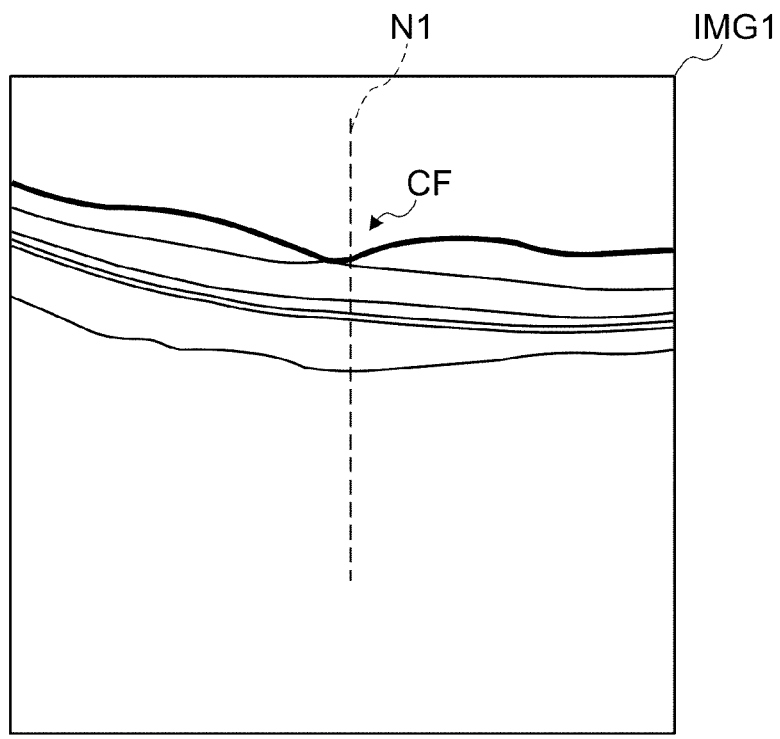
FIG. 4B is a schematic diagram for describing an operation of the ophthalmological imaging device according to the comparative examples of the embodiments.

FIGS. 4A and 4B show diagrams of comparative examples of the embodiments. FIG. 4A is an explanatory diagram of a fixation target coordinate system and a scanner coordinate system of the comparative examples. FIG. 4B schematically illustrates an OCT image captured by an ophthalmological imaging device of the comparative examples.

As shown in FIG. 4A, an origin of the scanner coordinate system SC is provided to coincide with the optical axis O of the objective lens 22. Such the position adjustment is performed in a designing phase, a shipping process, or a maintenance process. Thereby, in the ophthalmological imaging device according to the comparative examples, the alignment is performed so that the attention site of the subject's eye E is located at a position of the optical axis O.

Therefore, the frequency of photographing by scanning including the optical axis O becomes high.

However, as shown in FIG. 4B, reflection light from a vertex of a lens surface of the objective lens 22 may appear as an artifact N1 in the OCT image IMG1 obtained by scanning including the optical axis O. For example, despite photographing for the purpose of observing a tomographic image with the fovea centralis CF as the attention site as shown in FIG. 4B, the artifact N1 appears near the attention site, thereby it becomes difficult to observe near the attention site in the image. This phenomenon, i.e. artifacts due to the reflection from the optical system provided in the ophthalmological imaging device, is more likely to appear in the OCT image as coherence length becomes longer.

Therefore, OCT is performed with a position away from the optical axis O of the objective lens 22 as the control center of the optical scanner 42 in the embodiments.

Figure 5:
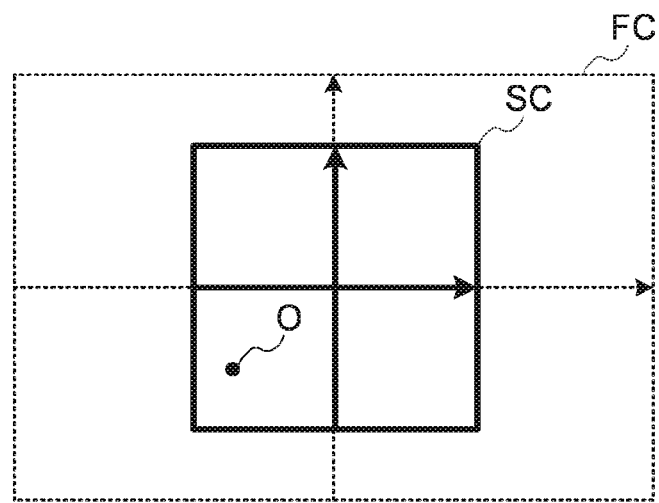
FIG. 5 is a schematic diagram for describing an operation of the ophthalmological imaging device according to the embodiments.

FIG. 5 is an explanatory diagram of the fixation target coordinate system and the scanner coordinate system according to the embodiments. Like reference numerals refer to like parts in FIGS. 4A and 5, and the same description may not be repeated.

As shown in FIG. 5, the optical scanner 42 is controlled so that a position away from the optical axis O of the objective lens 22 coincides with the origin of the scanner coordinate system SC. Thereby, an OCT image in which artifacts disappear near the attention site can be obtained. In particular, it becomes possible to observe near the attention site in detail in the OCT images (OCT images obtained by scanning including the optical axis O) which the frequency of photographing is high.

Further, the LCD 39 is controlled so that the origin of the scanner coordinate system SC coincides with the origin of the fixation target coordinate system FC in the embodiments. Thereby, artifact-free images by scanning frequently including fovea centralis can be obtained, by changing the display position of the fixation target by the LCD 39 to induce a fixation position of the subject's eye E.

In the embodiments, the main controller 211 controls the LCD 39 or the optical scanner 42 with an arbitrary position in the control coordinate system as the control center, by using the reference position information 212A and the adjustment information 212B described above. Thereby, not only artifacts due to the reflection light of the objective lens 22 but also artifacts due to the phenomenon of coherence revival occurred according to the state of the optical system can be removed. Incidentally, the origin of the scanner coordinate system SC and the origin of the fixation target coordinate system FC may be located at positions away from the optical axis O of the objective lens 22 in the designing phase.

In the following description, it is assumed that the initial positions and the amount of offset of the both coordinate systems included in the reference position information 212A are the same. That is, the main controller 211 changes the origin position of the fixation target coordinate system FC and the origin position of the scanner coordinate system SC by the same amount of offset in the same direction with respect to the optical axis O of the objective lens 22, with the origin of the fixation target coordinate system coinciding with the origin of the scanner coordinate system.

Figure 6:
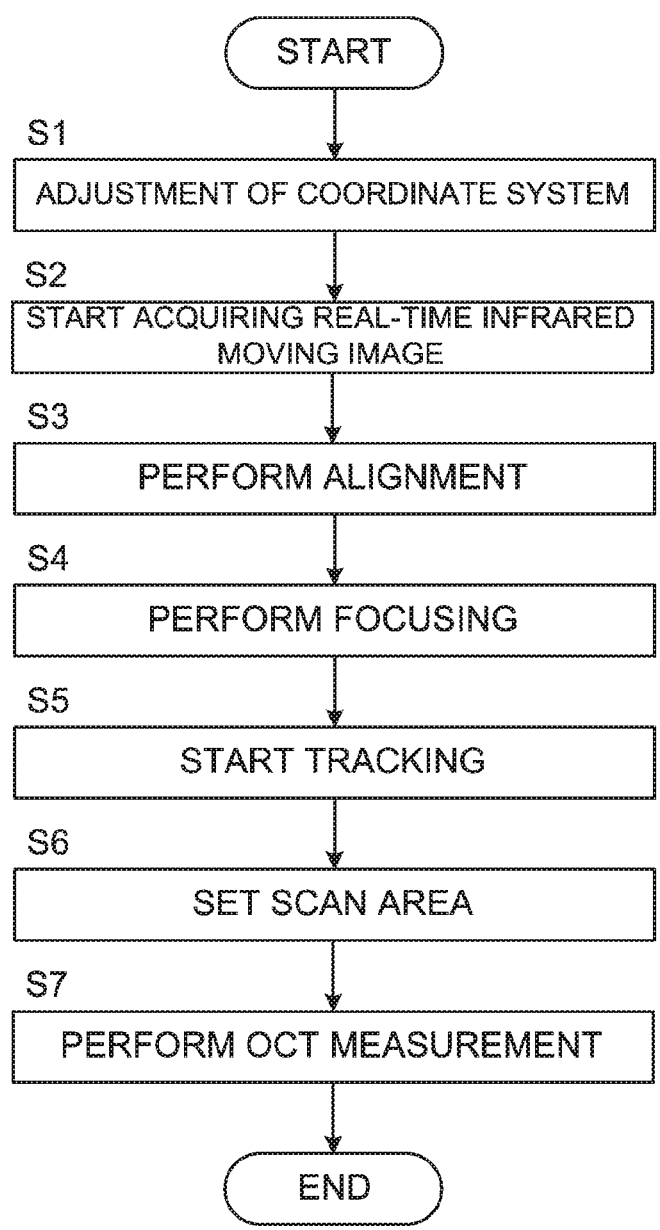
FIG. 6 is a flowchart illustrating a flow of an example of the operation of the ophthalmological imaging device according to the embodiments.

FIG. 6 illustrates an example of the operation of the ophthalmologic imaging device 1. This operation example includes position matching between the subject's eye E and the optical system of the device based on an image and setting of a scan area based on an image. The position matching includes alignment (automatic alignment), focusing (automatic focusing), and tracking (automatic tracking) for OCT measurement.

(S1)

First, the adjustment of the coordinate system is performed so that the origin of the fixation target coordinate system and the origin of the scanner coordinate system are located at a position away from the optical axis O of the objective lens 22. In S1, the decision of the adjustment information 212B and the storing of the decided adjustment information 212B to the storage 212 are performed.

For example, the main controller 211 controls the optical scanner 42 so that a position specified based on the reference position information 212A is located at the origin of the scanner coordinate system, to scan the fundus Ef for a predetermined scan area. The image forming part 220 forms an OCT image based on collected data acquired by sampling the detection result obtained by the detector 150. The formed OCT image is displayed on the display part 241. By setting the amount of offset ($\Delta x, \Delta y$) using the operation part 242 by the user while observing the OCT image displayed on the display part 241, the origin of the scanner coordinate system is changed. Next, the next OCT image is acquired in a state where the origin position of the scanner coordinate system, and the acquired OCT image is displayed on the display part 241, and this process is repeated. As a result, the user can decide the amount of offset deemed appropriate. The decided amount of offset is stored in the storage 212 as the adjustment information 212B.

Alternatively, for example, the data processor 230 may decide the amount of offset deemed appropriate, by determining presence/absence of artifacts by analyzing the interference signal based on the obtained OCT image or interference light, while increasing or decreasing the amount of offset by a predetermined step.

In S1, it is desirable that the amount of offset is determined as follows.

Figure 7:
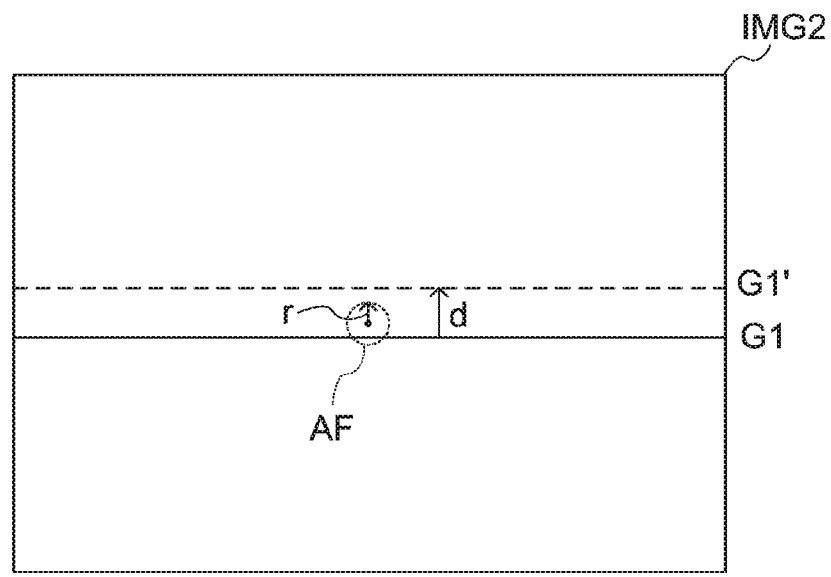
FIG. 7 is a schematic diagram for describing an operation of the ophthalmological imaging device according to the embodiments.

FIG. 7 is a diagram describing the amount of offset according to the embodiments. FIG. 7 schematically shows a projection image of the subject's eye E. In the projection image IMG2, an artifact AF is represented. Assuming that a radius of the artifact AF is r, it is desirable that the amount of offset $\Delta x$ and $\Delta y$ is larger than the radius r ($\Delta x > r$ and $\Delta y > r$). That is, the amount of displacement of the control center of the optical scanner 42 with respect to the optical axis O of the objective lens 22 is set based on the size of the artifact in the deflection direction of the measurement light LS by the optical scanner 42. In FIG. 7, the artifact AF appears in the tomographic image acquired in the scan line G1, but the artifact AF disappears in the tomographic image acquired in the scan line G1' shifted by d (d>r) in the y direction.

(S2)

Next, the fundus Ef is continuously irradiated with the illumination light from the observation light source 11 (near-infrared light through the action of the visible cut filter 14), thereby starting the acquisition of a near-infrared moving image of the subject's eye E. The near-infrared moving image is acquired in real time until the end of the continuous illumination. The frames of the moving image are temporarily stored in a frame memory (the storage 212) and sequentially sent to the data processor 230.

Incidentally, the alignment indicator and the split target are projected onto the subject's eye E respectively by the alignment optical system 50 and the focus optical system 60. Accordingly, the alignment indicator and the split target are represented in the near-infrared moving image. Alignment and focusing can be performed using them. The fixation target is also projected onto the subject's eye E by the LCD 39. The subject is instructed to fixate the eye on the fixation target.

(S3)

The data processor 230 sequentially analyzes the frames of the moving image of the subject's eye E to find the position of the alignment indicator, thereby calculating the movement amount of the optical system. The controller 210 controls the optical system driver (not illustrated) based on the movement amount of the optical system obtained by the data processor 230 to perform automatic alignment.

(S4)

The data processor 230 sequentially analyzes the frames of the moving image of the subject's eye E to find the position of the split target, thereby calculating the movement amount of the focusing lens 31. The controller 210 controls the photography focusing driver 31A based on the movement amount of the focusing lens 31 obtained by the data processor 230 to perform automatic focusing.

(S5)

Subsequently, the controller 210 starts the control for automatic tracking. Specifically, the data processor 230 analyzes the frames successively acquired by capturing a moving image of the subject's eye E with the optical system in real time, and monitors the movement (positional change) of the subject's eye E. The controller 210 controls the optical system driver (not illustrated) to move the optical system according to the position of the subject's eye E successively obtained. Thereby, the optical system can follow the movement of the subject's eye E in real time. Thus, it is possible to maintain a good positional relationship with proper alignment and focus.

(S6)

The controller 210 displays the near-infrared moving image on the display part 241 in real time. The user sets a scan area on the near-infrared moving image using the operation part 242. The scan area may be a one-dimensional region or a two-dimensional region.

If the scan mode of the measurement light LS and an attention site (optic papilla, macula, lesion, etc.) are set in advance, the controller 210 may set the scan area based on the content of the setting. Specifically, the attention site is specified by the image analysis of the data processor 230. Then, the controller 210 can set an area in a predetermined pattern to include the attention site (e.g., such that the attention site is located in the center).

(S7)

The controller 210 controls the light source unit 101 and the optical path length changing part 41 as well as controlling the optical scanner 42 based on the scan area set in S5 to perform OCT measurement of the fundus Ef.

As described above, the image forming part 220 forms a tomographic image (image) of a corresponding A-line based on collected data acquired by sampling detection signals obtained by the detector 150 based on the clock KC. If three-dimensional scan is set as the scan mode, the data processor 230 forms a three-dimensional image of the fundus Ef based on a plurality of tomographic images formed by the image forming part 220. With this, the operation example ends (END).

EXAMPLES OF MODIFICATIONS

First Modification Example

In the aforementioned embodiment, the case has been described in which the origin of the fixation target coordinate system FC and the origin of the scanner coordinate system SC are changed to a position away from the optical axis O of the objective lens 22. However, the configuration of the ophthalmological imaging device according to the embodiments is not limited thereto. For example, only the origin of the scanner coordinate system SC may be changed to a position away from the optical axis O of the objective lens 22.

Figure 8:
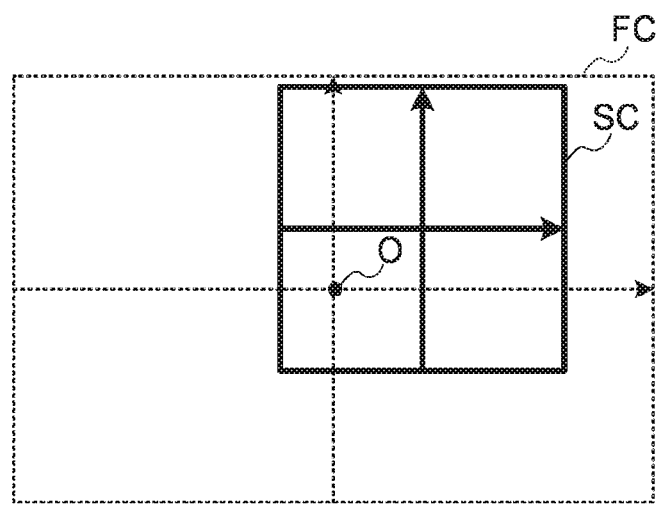
FIG. 8 is a schematic diagram for describing an operation of the ophthalmological imaging device according to examples of modifications of the embodiments.

FIG. 8 illustrates a diagram describing the fixation target coordinate system and the scanner coordinate system according to the first modification example of the embodiments. In FIG. 8, parts similarly configured to those in FIG. 5 are denoted by the same reference numerals, and the description thereof is omitted unless it is necessary.

As shown in FIG. 8, in the first modification example, the LCD 39 is controlled so that the position on the optical axis O of the objective lens 22 coincides with the origin of the fixation target coordinate system FC, and the optical scanner 42 is controlled so that the position away from the optical axis O coincides with the origin of the scanner coordinate system SC. According to the first modification example, an OCT image in which artifacts disappeared near the attention site can be obtained, similarly to the above embodiments.

Second Modification Example

Figure 9:
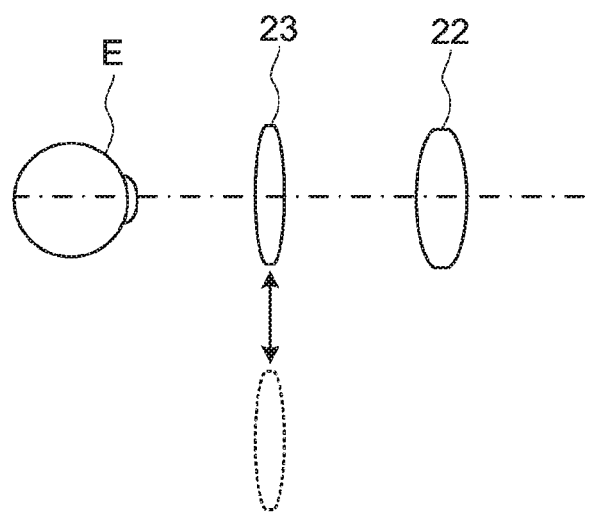
FIG. 9 is a schematic diagram for describing the ophthalmological imaging device according to examples of modifications of the embodiments.

FIG. 9 shows main parts of the configuration of the ophthalmological imaging device according to the second modification example of the embodiments. In FIG. 9, only the configuration between the subject's eye E and the objective lens 22 is shown.

The ophthalmological imaging device according to the second modification example includes a front lens 23 capable of being arranged between the objective lens 22 and the subject's eye E. The front lens 23 can be manually or automatically arranged between the objective lens 22 and the subject's eye E. In the case that the front lens 23 is arranged between the objective lens 22 and the subject's eye E, the present invention can be applied by replacing the "objective lens" in the aforementioned embodiments with the "front lens" regarding to the control with respect to the coordinate system. For example, in the case that the front lens 23 is arranged between the objective lens 22 and the subject's eye E, the main controller can control the optical scanner 42 so as to deflect the measurement light around a position away from the optical axis of the front lens 23. In the same way, the main controller can control the LCD 39 so that a position away from the optical axis of the front lens 23 coincides with the origin of the fixation target coordinate system.

[Effects]

The effects of the ophthalmological imaging device according to the embodiments will be described.

An ophthalmological imaging device (ophthalmological imaging device 1) according to the embodiments comprises an objective lens (objective lens 22), an interference optical system (optical system from the OCT unit 100 to the relay lens 45), an optical scanner (optical scanner 42), a controller (controller 210, main controller 211), and an image forming part (image forming part 220). The interference optical system divides light (light L0) from a light source (light source unit 101) into measurement light (measurement light LS) and reference light (reference light LR), causes the measurement light to become incident on a subject's eye (subject's eye E) via the objective lens, and detects interference light (interference light LC) between the reference light and return light of the measurement light that has exited from the subject's eye and passed through the objective lens. The optical scanner deflects the measurement light. The controller controls the optical scanner such that a position away from an optical axis (optical axis O) of the objective lens is set as a center to deflect the measurement light. The image forming part forms an image of the subject's eye based on a detection result of the interference light by the interference optical system.

According to such a configuration, an image of a subject's eye in which artifacts disappear near an attention site can be obtained. In particular, it becomes possible to observe near the attention site in detail in an image which the frequency of photographing is high such as including the optical axis of the objective lens. In addition, not only artifacts due to reflection light of the objective lens but also artifacts due to the phenomenon of coherence revival occurred according to the state of the optical system can be removed.

Further, the ophthalmological imaging device according to the embodiments comprises a fixation target projection system (optical system from the LCD 39 to the dichroic mirror 46) that projects a fixation target onto a fundus (fundus Ef) of the subject's eye, wherein the controller may perform a control of the optical scanner and a control of the fixation target projection system.

According to such a configuration, it becomes possible to observe near the attention site in detail at a position away from an appearance position of the artifacts due to the reflection light of the objective lens, by moving a fixation position of the subject's eye.

Further, in the ophthalmological imaging device according to the embodiments, the fixation target projection system comprises a light emitting part (LCD 39) configured to be capable of changing a light emitting position, wherein the fixation target projection system projects light from the light emitting part onto the fundus of the subject's eye, the ophthalmological imaging device may comprise a storage (storage 212) that previously stores light emitting position information (reference position information 212A) representing a light emitting position by the light emitting part, and the controller may change the light emitting position information and performs the control of the fixation target projection system.

According to such a configuration, a display position of the fixation target can be changed depending on the control of the optical scanner with simple configuration and control.

Further, in the ophthalmological imaging device according to the embodiments, the controller may change the light emitting position information depending on a displacement of a control center of the optical scanner with respect to the optical axis of the objective lens.

According to such a configuration, an artifact-free image by scanning frequently including fovea centralis can be obtained, by changing the display position of the fixation target to induce the fixation position of the subject's eye.

Further, in the ophthalmological imaging device according to the embodiments, an amount of the displacement ($\Delta x$ or $\Delta y$) of the control center of the optical scanner with respect to the optical axis of the objective lens may be set based on a size (radius r) of an artifact in a direction of deflection of the measurement light by the optical scanner.

According to such a configuration, an image in which artifacts disappear can be obtained with high likelihood.

Further, the ophthalmological imaging device according to the embodiments may comprise a front lens configured to be capable of being located between the objective lens and the subject's eye, wherein when the front lens is located between objective lens and the subject's eye, the controller may control the optical scanner such that the position away from the optical axis of the front lens is set as the center to deflect the measurement light.

According to such a configuration, it becomes possible to observe near the attention site in detail in the image which the frequency of photographing is high such as including the optical axis of the front lens. In addition, not only artifacts due to reflection light of the front lens but also artifacts due to the phenomenon of coherence revival occurred according to the state of the optical system can be removed.

Configurations described above are merely examples for preferably implementing the present invention. Therefore, arbitrary modifications (omission, replacement, addition, etc.) may be applied within the scope of the invention. The configuration to be employed is selected according to the purpose, for example. In addition, depending on the configuration to be employed, actions and effects obvious to those skilled in the art and the actions and the effects described in this specification can be achieved.

What is claimed is:

1. An ophthalmological imaging device comprising:
   an objective lens;
   an interference optical system that divides light from a light source into measurement light and reference light, causes the measurement light to become incident on a subject's eye via the objective lens, and detects interference light between the reference light and return light of the measurement light that has exited from the subject's eye and passed through the objective lens;
   an optical scanner that deflects the measurement light;
   a controller that controls the optical scanner such that a position away from an optical axis of the objective lens is set as a center to deflect the measurement light; and
   an image forming part that forms an image of the subject's eye based on a detection result of the interference light by the interference optical system,
   wherein the measurement light is deflected by displacing a control center of the optical scanner, and an amount of the displacement of the control center of the optical scanner with respect to the optical axis of the objective lens is set based on a size of an artifact in a direction of deflection of the measurement light by the optical scanner.

2. The ophthalmological imaging device of claim 1, further comprising a fixation target projection system that projects a fixation target onto a fundus of the subject's eye, wherein
   the controller performs a control of the optical scanner and a control of the fixation target projection system.

3. The ophthalmological imaging device of claim 2, wherein the fixation target projection system comprises a light emitting part configured to be capable of changing a light emitting position, wherein the fixation target projection system projects light from the light emitting part onto the fundus of the subject's eye,
   the ophthalmological imaging device comprises a storage that previously stores light emitting position information representing a light emitting position by the light emitting part, and
   the controller changes the light emitting position information and performs the control of the fixation target projection system.

4. The ophthalmological imaging device of claim 3, wherein the controller changes the light emitting position information depending on a displacement of a control center of the optical scanner with respect to the optical axis of the objective lens.

5. The ophthalmological imaging device of claim 1, further comprising a front lens configured to be capable of being located between the objective lens and the subject's eye, wherein
    when the front lens is located between objective lens and the subject's eye, the controller controls the optical scanner such that the position away from the optical axis of the front lens is set as the center to deflect the measurement light.

\* \* \* \* \*